US010080505B2

(12) United States Patent
Sano et al.

(10) Patent No.: US 10,080,505 B2
(45) Date of Patent: Sep. 25, 2018

(54) ELECTROCARDIOGRAPH AND BIOELECTRODE PAD

(75) Inventors: Yoshihiko Sano, Osaka (JP); Masahide Harada, Hokkaido (JP)

(73) Assignees: NIPRO CORPORATION, Osaka (JP); HARDA ELECTRONICS CO., LTD, Hokkaido (JP)

( * ) Notice: Subject to any disclaimer, the term of this patent is extended or adjusted under 35 U.S.C. 154(b) by 895 days.

(21) Appl. No.: 14/355,418

(22) PCT Filed: Nov. 2, 2011

(86) PCT No.: PCT/JP2011/075313
§ 371 (c)(1),
(2), (4) Date: Apr. 30, 2014

(87) PCT Pub. No.: WO2013/065147
PCT Pub. Date: May 10, 2013

(65) Prior Publication Data
US 2014/0288407 A1 Sep. 25, 2014

(51) Int. Cl.
A61B 5/0428 (2006.01)
A61B 5/0408 (2006.01)
A61B 5/00 (2006.01)

(52) U.S. Cl.
CPC ........ *A61B 5/04085* (2013.01); *A61B 5/0428* (2013.01); *A61B 5/04087* (2013.01); *A61B 5/7214* (2013.01); A61B 2562/125 (2013.01)

(58) Field of Classification Search
CPC ............ A61B 5/04085; A61B 5/04002; A61B 5/7214; A61B 1/04; A61B 1/0476;
(Continued)

(56) References Cited

U.S. PATENT DOCUMENTS 4,583,548 A * 4/1986 Schmid ................ A61B 5/0408
600/396
5,466,256 A * 11/1995 McAdams ........... A61N 1/0492
600/391
(Continued)

FOREIGN PATENT DOCUMENTS

CN        2259857 Y      8/1997
JP     2006-231020 A     9/2006
WO   WO 2008/152588 A2  12/2008

OTHER PUBLICATIONS

PCT International Search Report dated Jan. 24, 2012, which was issued in a related PCT International Application No. PCT/JP2011/075313 (5 pages).
(Continued)

*Primary Examiner* — Eunhwa Kim
(74) *Attorney, Agent, or Firm* — Robert P. Michal, Esq.; Carter, DeLuca, Farrell & Schmidt, LLP

(57) ABSTRACT

An electrocardiograph measures an electrocardiac signal by processing electric signals detected by bioelectrode pads. The bioelectrode pads each includes a plurality of sheets of electrodes disposed by being stacked on each other; conductive gel sheets disposed alternately with the sheets of electrodes and interposed between the electrodes; and a dynamic pressure stabilizing plate. The electrocardiograph includes a first differential circuit for obtaining an electrocardiac source signal by taking the difference between signals each obtained from any one of the electrodes of each of two bioelectrode pads; a second differential circuit for obtaining a body motion noise signal by taking the difference between signals obtained from any two of the electrodes of each of said two bioelectrode pads; and a body motion noise removing circuit for removing the low frequency components of the body motion noise signal of each of said two bioelectrode pads from the electrocardiac source signal.

5 Claims, 5 Drawing Sheets

(58) Field of Classification Search
CPC ......... A61B 5/721; A61B 5/0006; A61B 5/04; A61B 5/04012; A61B 5/0402; A61B 5/04021; A61B 5/04023; A61B 5/0408; A61B 5/04087
See application file for complete search history.

(56) References Cited

U.S. PATENT DOCUMENTS 5,704,365 A 1/1998 Albrecht et al.
6,961,601 B2 * 11/2005 Matthews ............ A61B 5/0408
600/372

OTHER PUBLICATIONS

Communication (Extended European Search Report) dated Jun. 5, 2015 issued by the European Patent Office in related European Application No. 11875094.2 (8 pages).
L.A. Geddes, et al. "The Use of Liquid-Junction Electrodes in Recording the Human Electrocardiogram (ECG)", J. Electrocardiology, 1968, 1(1), pp. 51-56 (5 pages).
A. Gruetzmann et al. "Novel dry electrodes for ECG monitoring", Physiological Measurements, 2007, vol. 28, pp. 1375-1390 (16 pages).
E. Huigen et al. "Investigation into the origin of the noise of surface electrodes", 2002, Medical & Biological Engineering & Computing, vol. 40, pp. 332-338, (7 pages).
E.T. McAdams, et al. "Factors affecting electrode-gel-skin-interface impedance in electrical impedance tomography", 1996, Medical & Biological Engineering & Computing, vol. 34, pp. 397-408, (12 pages).
A, Searle et al. "A direct comparison of wet, dry and insulating bioelectric recording electrodes", Physiol. Meas. 2000, vol. 21, pp. 271-283 (13 pages).
PCT International Preliminary Report on Patentability and Written Opinion of the International Searching Authority dated May 13, 2014, which was issued in a related PCT International Application No. PCT/JP2011/075313 (6 pages).
Communication (Office Action) dated Mar. 31, 2015 issued by the Chinese Intellectual Patent Office in related Chinese Patent Application No. 201180074541.3 (6 pages).

* cited by examiner

[FIG.1(a)]
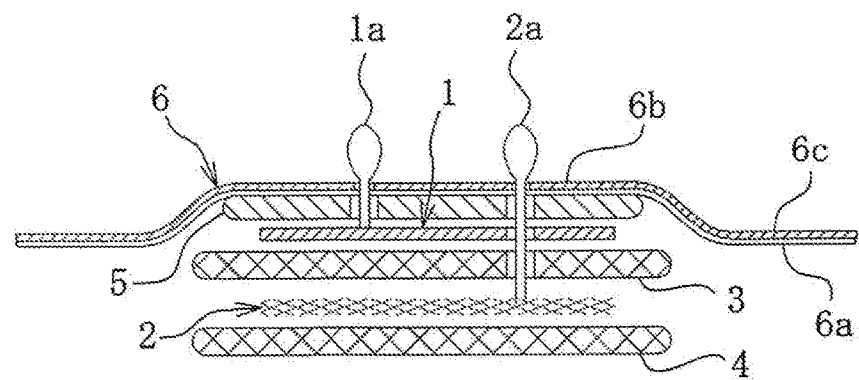
[FIG.1(b)]
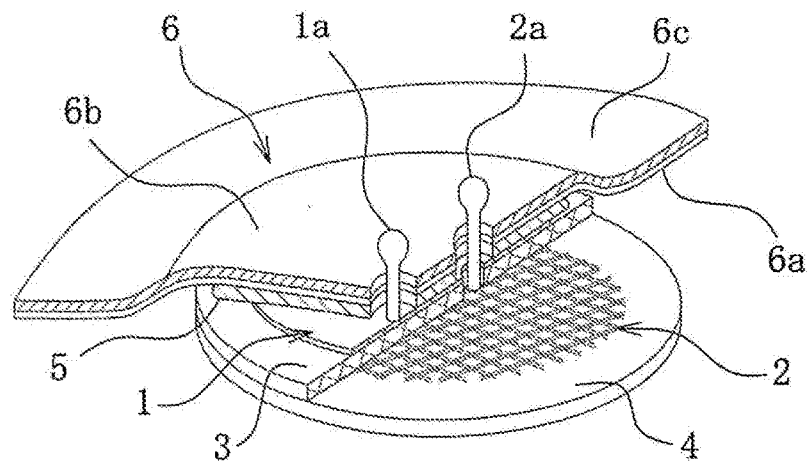

[FIG.2]
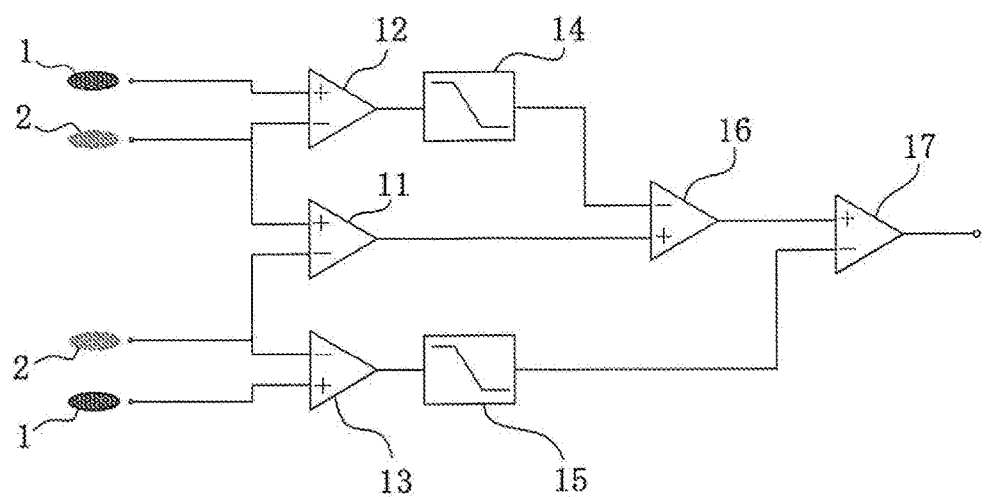
[FIG.3(a)]
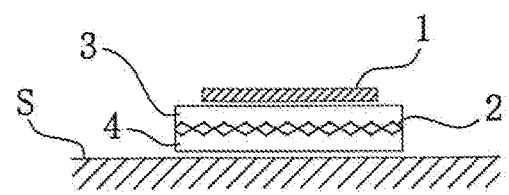
[FIG.3(b)]
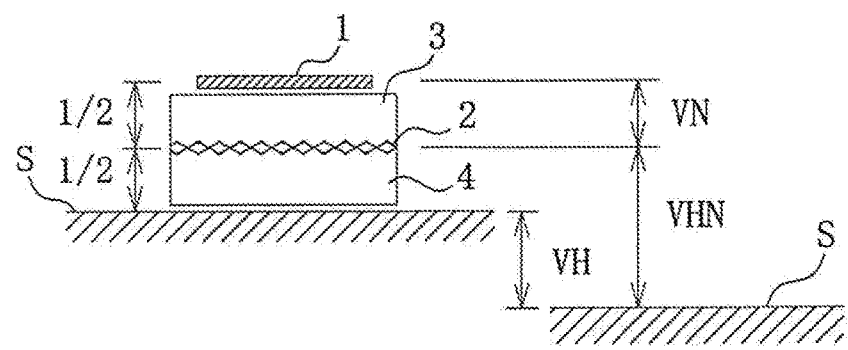

[FIG.4(a)]
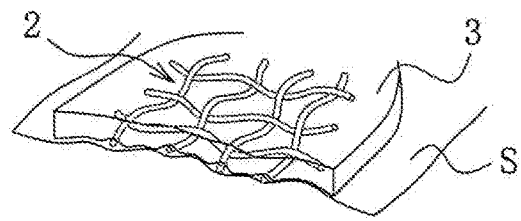
[FIG.4(b)]
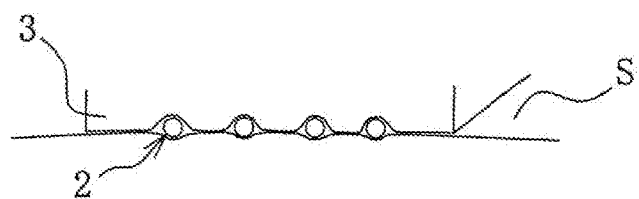
[FIG.5]
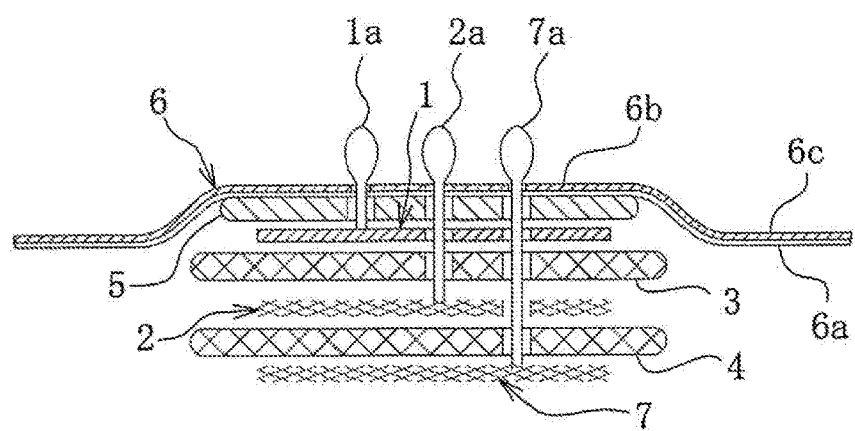

[FIG.6]
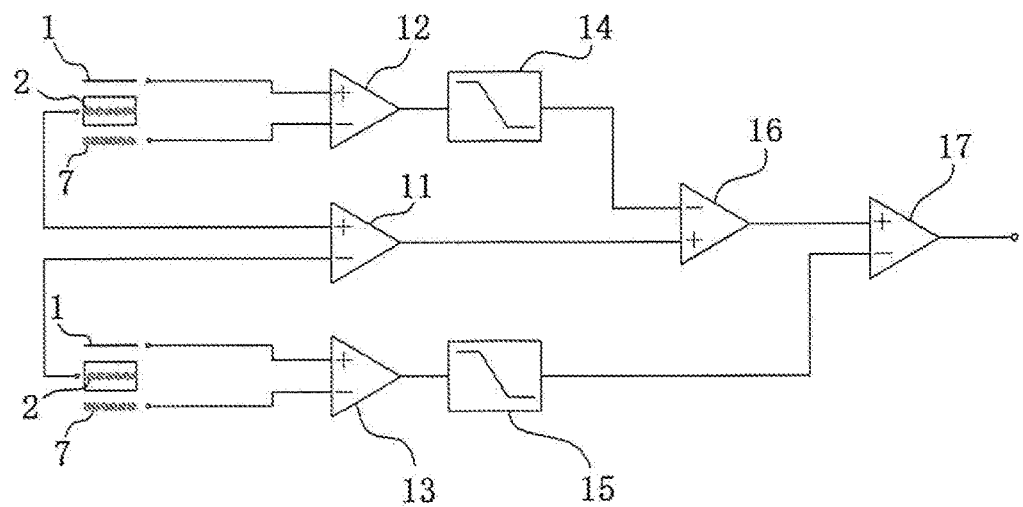
[FIG.7]
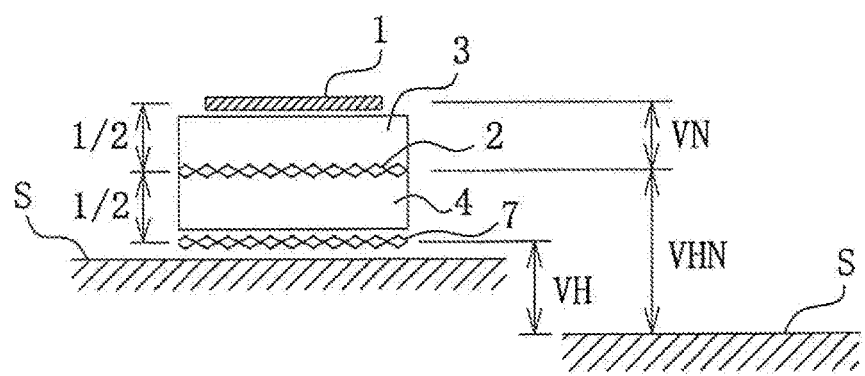

[FIG.8]
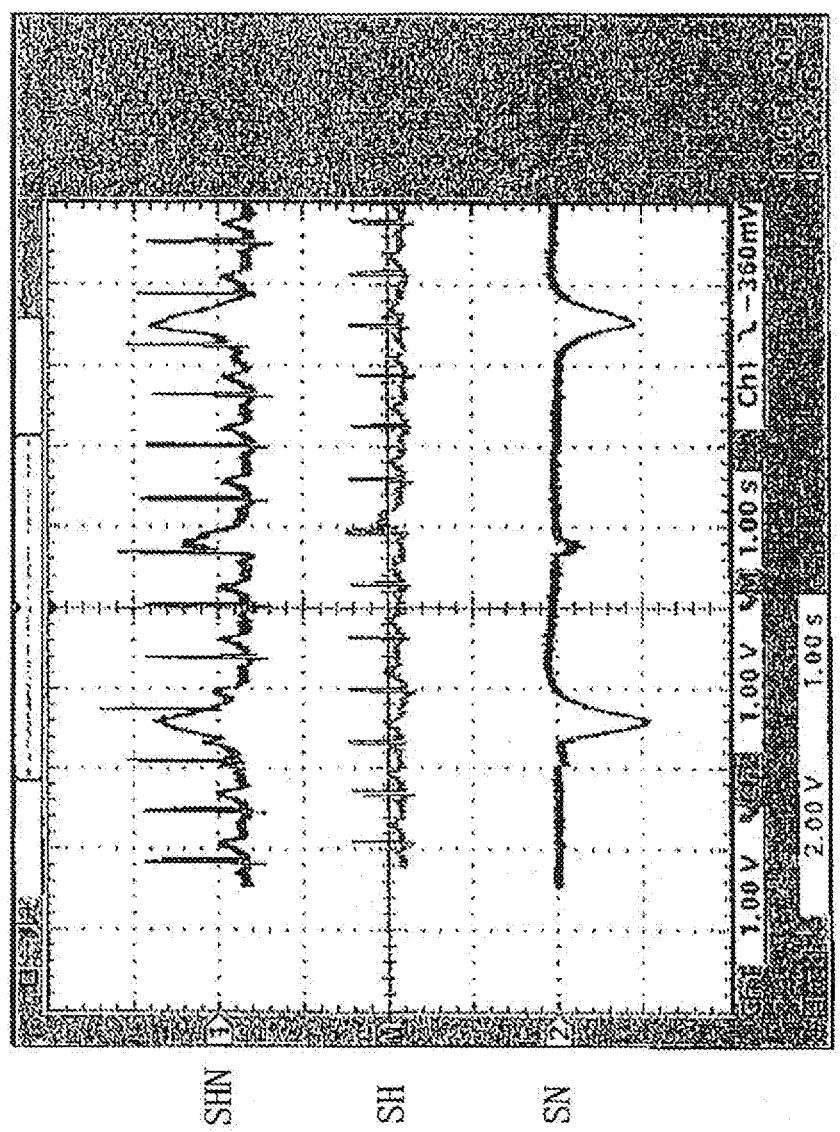

ELECTROCARDIOGRAPH AND BIOELECTRODE PAD

CROSS REFERENCE TO RELATED APPLICATIONS

This application is a U.S. National Phase Application under 35 USC 371 of International Application No. PCT/JP2011/075313 filed Nov. 2, 2011, the entire disclosure of which is incorporated herein by reference.

TECHNICAL HELD

The present invention relates to an electrocardiograph and a bioelectrode pad which is used for the electrocardiograph and is applied to a skin of a living body for measuring an electrocardiac signal. Particularly, the present invention relates to the electrocardiograph and the bioelectrode pad which can stably measure the electrocardiac signal without being disturbed by a body motion noise.

BACKGROUND INFORMATION

The conventional electrocardiograph and the bioelectrode pad are known for example from a patent document 1 which is previously proposed by an applicant of this patent application. In the electrocardiograph mentioned above, it is possible to measure the electrocardiac signal without being disturbed by the body motion noise by: using a plurality of bioelectrode pads each having a plurality of electrodes having different areas respectively which are contacted with a skin surface of a specific portion of living body respectively; measuring an original electrocardiac signal by contacting the bioelectrode pads with the skin surface of living body and obtaining a difference between signals supplied from either one electrodes of these bioelectrode pads; measuring a signal of the body motion noise by obtaining a difference between a signal supplied from the electrode having a relatively small area and a signal supplied from the electrode having a relative large area, with respect to respective bioelectrode pads; and removing a low frequency component of the signal of the body motion noise from the original electrocardiac signal. In this case, the signal of the body motion noise is generated, since a polarization potential and impedance, which generate between the electrode and a conductive gel or between the conductive gel and the skin surface, are varied due to the body motion.

PRIOR ART TECHNICAL DOCUMENTS

Patent Documents

Patent Document 1: Japanese Patent Laid-Open Publication No. 2006-231020

SUMMARY

Task to be Solved by the Invention

Meanwhile, where the inventors according to the invention further investigated the conventional electrocardiograph and the bioelectrode pad mentioned above, tasks such as the following were newly found. That is, in the conventional bioelectrode pad, since the signal of the body motion noise is obtained by an area difference of the electrodes, it is not always possible to obtain the signal of the body motion noise having a sufficient level from the electrode having a small area due to an practical size limitation of the bioelectrode pad. Therefore, in the conventional electrocardiograph utilizing the bioelectrode pad mentioned above, since it is difficult to set a gain of the signal of the body motion noise, it is not possible to sufficiently eliminate an effect of the body motion from the electrocardiac signal.

Then, as a result that the tasks mentioned above are further investigated, it is confirmed that the signal of the body motion noise and the original electrocardiac signal can be obtained in a sufficient level respectively by stacking a plurality of electrodes in a thickness direction via the conductive gel sheet therebetween.

Solution for Task

The present invention is intended to solve the tasks of the conventional electrocardiograph and bioelectrode pad with taking into consideration of the findings mentioned above advantageously. An electrocardiograph according to the invention relates to an electrocardiograph for measuring an electrocardiac signal by processing an electrical signal detected by using a plurality of bioelectrode pads which are applied to a skin of a living body, wherein the plurality of bioelectrode pads each comprises: plural sheets of electrodes stacked mutually; and conductive gel sheets arranged alternately with the plural sheets of electrodes and interposed between the electrodes; and wherein the electrocardiograph comprises: a first difference circuit for determining an original electrocardiac signal by obtaining a difference between signals supplied from either one electrodes of each of two bioelectrode pads among the plurality of bioelectrode pads; a second difference circuit for determining a body motion noise signal by obtaining a difference between signals supplied from either two of the electrodes of the respective two bioelectrode pads; and a body motion noise removing circuit for removing a low frequency component of the body motion noise signals supplied from respective two bioelectrode pads from the original electrocardiac signal.

Moreover, according to the invention, a bioelectrode pad for the electrocardiograph mentioned above, comprises: plural sheets of electrodes stacked mutually; and conductive gel sheets arranged alternately with the plural sheets of electrodes and interposed between the electrodes.

Effect of the Invention

In the electrocardiograph and the bioelectrode pad mentioned above, if the bioelectrode pad is fitted to a surface of the skin at a specified portion of the living body, the plural sheets of the electrodes of the bioelectrode pad are pressed to the skin surface in such a manner that the electrodes are stacked with each other and the conductive gel is interposed between the electrodes. Therefore, the electrodes are connected in series with each other and it is possible to detect and output a signal by utilizing the electrode having a sufficient area. In this manner, voltages of the signals output from the electrodes sandwiched between the electrode and the skin are decreased by a predetermined ratio defined by the number of the sheets of the electrodes and the conductive gel sheets with respect to a voltage of the signal output from the outer electrode positioned on an outside opposite to a skin side.

Therefore, according to the bioelectrode pad of the present invention, for example, there may be a case that the outer electrode positioned opposite to the skin side is made to be a body motion noise detection electrode and also the electrode sandwiched between the electrode and the skin is made to be an original electrocardiac signal detection electrode, or, there may be a case that the outer electrode positioned opposite to the skin side is made to be the original electrocardiac signal detection electrode and also the electrode sandwiched between the electrode and the skin is made to be the body motion noise detection electrode. In the embodiments mentioned above, it is possible to detect a body motion noise signal and an original electrocardiac signal each having a sufficient level by utilizing these electrodes. Moreover, it is possible to make the signal from the electrode sandwiched between the electrode and the skin to a value decreased by a predetermined ratio defined by the number of sheets of the electrodes and the conductive gel sheets, with respect to the voltage of the signal output from the outer electrode positioned opposite to the skin side.

Moreover, according to the electrocardiograph of the present invention which utilizes the bioelectrode pad of the present invention, it is possible to obtain the body motion noise signal and the original electrocardiac signal each having a sufficient level mentioned above. In addition, it is possible to easily perform a gain setting of the body motion noise or the original electrocardiac signal. Therefore, it is possible to easily remove an influence of the body motion from the electrocardiac signal.

In addition, in the electrocardiograph according to the present invention, the followings are preferable. That is, the two bioelectrode pads mentioned above have respectively three sheets of the electrodes stacked mutually. The first difference circuit mentioned above obtains a difference between the signals supplied from the electrode positioned at an intermediate portion among three sheets of the electrodes to obtain the original electrocardiac signal. The second difference circuit mentioned above obtains a difference between the signals supplied from the electrodes positioned at both sides of three sheets of the electrodes to obtain the body motion noise signal.

In the preferable embodiment mentioned above, since one of the electrodes positioned at both side portions is the electrode positioned nearest to the skin surface and the other is the electrode positioned most far from the skin surface, a voltage of the body motion noise signal can be detected between the electrodes positioned at both side portions, and a voltage of the original electrocardiac signal and a voltage having ½ level of the body motion noise signal can be detected between the electrodes positioned at an intermediate portion. Therefore, all body motion noise signal supplied from the electrodes positioned at an intermediate portion can be detected by the electrodes positioned at both side portions, and thus it is possible to effectively remove the body motion noise signal from the original electrocardiac signal at respective bioelectrode pads.

Meanwhile, in the bioelectrode pads according to the present invention, it is preferable to further arrange a conductive gel sheet in a stacked manner outside of the plural sheets of the electrodes, which is also arranged at the skin side and in the stacked direction of the plural sheets of the electrodes.

According to the preferable embodiment mentioned above, since the conductive gel sheet is interposed between the skin surface and the electrode positioned nearest to the skin surface, it is possible to detect the body motion noise signal even at the electrode positioned nearest to the skin surface, and also it is possible to cover the electrodes by the conductive gel sheet.

Moreover, in the bioelectrode pad according to the present invention, it is preferable to form the electrode at least sandwiched by the conductive gel sheets among the plural sheets of the electrodes mentioned above in a net-like shape or in a porous shape such as fabric or the like.

According to the preferable embodiment mentioned above, since the conductive gel is penetrated through the net-like electrode or the porous electrode, properties of the conductive gel sheets arranged at both sides of the electrode become even. Therefore, in the electrocardiograph, it is possible to easily perform the gain settings of the body motion noise and the original electrocardiac signal. Moreover, a contact area between the electrode and the conductive gel sheet becomes larger as compared with a plane electrode, and further the electrode is deformed flexibly along the skin surface. Therefore, it is possible to improve a detection level of the signal also from this point.

Then, in the bioelectrode pad according to the present invention, it is preferable to further comprise a fitting sheet having: an intermediate portion for supporting the electrodes and the conductive gel sheets in a stacked condition, which is stacked outside of the electrode at an opposite side with respect to the skin side and in an stacked direction of the plural sheets of electrodes; and an end portion for fitting the electrodes and the conductive gel sheets supported by the intermediate portion to a skin surface at a predetermined portion of the living body, which is continued with the intermediate portion, positioned outside of the electrodes and the conductive gel sheets in an extended direction of the plural sheets of electrodes, and has an adhesive surface.

According to the preferable embodiment mentioned above, the electrodes and the conductive gel sheets are supported in a stacked condition by the intermediate portion of the fitting sheet, which is stacked outside of the electrode at an opposite side with respect to the skin side and in a stacked direction of the plural sheets of electrodes. Moreover, the electrodes and the conductive gel sheets supported by the intermediate portion are fitted to the skin surface at a predetermined portion of the living body by the end portion which is positioned outside of the electrodes and the conductive gel sheets in an extended direction of the plural sheets of electrodes, and has an adhesive surface. Therefore, it is possible to securely maintain the electrode and the conductive gel sheet in a staked condition on the skin surface of the predetermined portion of the living body.

BRIEF DESCRIPTION OF THE DRAWINGS

FIGS. 1 (a) and (b) are a cross-sectional view and a partially-cutout perspective view respectively showing one embodiment of a bioelectrode pad according to the present invention.

FIG. 2 is a block diagram illustrating a construction of one embodiment of an electrocardiograph according to the present invention which utilizes the bioelectrode pad of the embodiment mentioned above.

FIG. 3 (a) is a schematic view depicting a construction of the bioelectrode pad of the embodiment mentioned above in a simplified manner, and (b) is a schematic view showing a function of the bioelectrode pad of the embodiment mentioned above.

FIGS. 4 (a) and (b) are a partially-cutout perspective view and a cross-sectional view respectively illustrating one modified embodiment of the bioelectrode pad of the embodiment mentioned above.

FIG. 5 is a cross-sectional view depicting another embodiment of the bioelectrode pad according to the present invention.

FIG. 6 is a block diagram showing a construction of another embodiment of the electrocardiograph according to the present invention which utilizes the bioelectrode pad of the embodiment mentioned above.

FIG. 7 is a schematic view illustrating a function of the bioelectrode pad of the embodiment mentioned above.

FIG. 8 is a schematic view depicting a measurement result of an electrocardiac signal by means of the electrocardiograph of the embodiment mentioned above.

EMBODIMENT FOR CARRYING OUT THE INVENTION

Hereinafter, embodiments for carrying out the present invention will be explained in detail with reference to the drawings by specific embodiments. FIGS. 1(a) and 1(b) are a cross-sectional view and a partially-cutout perspective view respectively showing one embodiment of a bioelectrode pad according to the present invention.

A bioelectrode pad according to this embodiment comprises: as shown in FIG. 1, two sheets of electrodes 1, 2 stacked mutually; two conductive gel sheets 3, 4 arranged alternately with the two sheets of electrodes 1, 2, wherein one conductive gel sheet is interposed between the electrodes 1 and 2 and the other conductive gel sheet is interposed outside of the electrode 2 at a skin side (lower side in the figure); and a dynamic pressure stabilizing plate 5 stacked outside of the two sheets of electrodes 1, 2 (upper side in the figure), which is an opposite side of the skin side in a stacked direction of the two sheets of electrodes 1, 2. In addition, the bioelectrode pad further comprises a fitting sheet 6 for fitting the dynamic pressure stabilizing plate 5, the electrodes 1, 2 and the conductive gel sheets 3, 4 to a skin surface not shown of a predetermined portion of a living body positioned at a lower side of the members mentioned above in the figure under a stacked condition.

The fitting sheet 6 is made of a normal nonconductive material and has a substantially circular shape. Moreover, the fitting sheet 6 has an adhesive layer 6a arranged on all rear surface (lower surface in the figure). Further, the fitting sheet 6 comprises: an intermediate portion 6b for supporting the dynamic pressure stabilizing plate 5, the electrodes 1, 2 and the conductive gel sheets 3, 4 in a stacked condition by means of the adhesive layer 6a, which is stacked outside of the dynamic pressure stabilizing plate 5 (upper side in the figure) at an opposite side with respect to the skin side in a stacked direction of the two sheets of electrodes 1, 2; and an external end portion 6c for fitting the dynamic pressure stabilizing plate 5, the electrodes 1, 2 and the conductive gel sheets 3, 4 supported by the intermediate portion 6b to the skin surface not shown at a predetermined portion of the living body positioned at a lower side in the figure by means of the adhesive layer 6a, which is continued with the intermediate portion 6b and is positioned outside of the dynamic pressure stabilizing plate 5, the electrodes 1, 2 and the conductive gel sheets 3, 4 in an extended direction (horizontal direction in the figure) of the two sheets of electrodes 1, 2.

Here, it is preferable that the electrode 1 is used as a detection electrode for a body motion noise signal since the conductive gel sheet 3 is interposed between the electrodes 1 and 2 and thus a noise generated from the conductive gel due to a body motion is large. Moreover, it is preferable that the electrode 2 is used as a detection electrode for an original electrocardiac signal since a distance between the skin surface and the electrode 2 is lesser than that of the electrode 1. However, if the electrode 1 is used as the detection electrode for the original electrocardiac signal and the electrode 2 is used as the detection electrode for the body motion noise signal, it is possible to detect the body motion noise signal and the original electrocardiac signal.

The dynamic pressure stabilizing plate 5 is formed by a substrate made of for example plastic as a whole and has a substantially disc-like shape. Moreover, the electrode 1 is formed by a substrate made of for example plastic as a whole and having a substantially planar shape, and has a connection terminal 1a projected upward from its upper surface. Further, the planar portion and a surface of the connection terminal 1a are coated by a plating of for example silver chloride which is a high-conductive material, and an outer surface of a shaft portion of the connection terminal 1a of the electrode 1 is coated by an insulating material. Furthermore, a tip portion of the connection terminal 1a is projected at a surface side of the fitting sheet 6 by penetrating it from a rear side via a through hole of the dynamic pressure stabilizing plate 5 and a through hole of the intermediate portion 6b of the fitting sheet 6.

On the other hand, the electrode 2 is formed by for example metal wires as a whole and having a substantially net-like shape, and has a connection terminal 2a projected upward from its upper surface. Moreover, the net-like portion and a surface of the connection terminal 2a are coated by a plating of for example silver chloride which is a high-conductive material, and an outer surface of a shaft portion of the connection terminal 2a of the electrode 2 is coated by an insulating material. Further, a tip portion of the connection terminal 2a is projected at a surface side of the fitting sheet 6 by penetrating it from a rear side via through holes of the conductive gel sheet 3, the electrode 1 and the dynamic pressure stabilizing plate 5 and a through hole of the intermediate portion 6b of the fitting sheet 6.

The conductive gel sheets 3, 4 are made of a normal gel sheet having a disc-like shape respectively larger than the electrodes 1, 2 and having an adhesion. The conductive gel sheet 3 is stuck to the dynamic pressure stabilizing plate 5 at its peripheral portion, and the electrode 1 is fixed by sandwiching it between the conductive gel sheet 3 and the dynamic pressure stabilizing plate 5. The conductive gel sheet 4 is stuck to the conductive gel sheet 3 at its peripheral portion, and the electrode 2 is fixed by sandwiching it between the conductive gel sheets 3 and 4.

Further, in the bioelectrode pad of this embodiment, in order to cover and protect whole portions of the adhesive layer 6a of the external end portion 6c of the fitting sheet 6 mentioned above and the outer conductive gel sheet 4, a peeling sheet not shown made of a normal film, to which a surface treatment is performed, is arranged so as to be easily peel off from the adhesive layer 6a and the conductive gel sheet 4.

FIG. 2 is a block diagram showing one embodiment of the electrocardiograph according to the present invention which utilizes the bioelectrode pad of the embodiment mentioned above. The electrocardiograph of this embodiment, as shown in FIG. 2, comprises: a first differential amplifier 11 as a first difference circuit, which obtains a difference between the signals supplied from the electrodes 2 of each of the two bioelectrode pads of the embodiment mentioned above, amplifies the difference and outputs the amplified difference as the original electrocardiac signal; two second differential amplifiers 12, 13 as two second difference circuits, which obtain a difference between the signals supplied from the electrodes 1 and 2 of each of the two bioelectrode pads, amplify the difference and output the amplified difference as the body motion noise signal respectively; and a body motion noise removing circuit made of two low-pass filters (for example, filters having a cut-off frequency of 40 Hz) 14, 15 for deriving low frequency components of respective body motion noise signals of two bioelectrode pads mentioned above which are output from these two differential amplifiers 12, 13, and two differential amplifiers 16, 17 which amplify and output a signal obtained by removing these low frequency components of the body motion noise signal from the original electrocardiac signal.

In the bioelectrode pad of the embodiment mentioned above, if the bioelectrode pad is applied to a skin surface S of a predetermined portion of the living body as shown in FIG. 3(a), the two sheets of electrodes 1, 2 of the bioelectrode pad are pressed to the skin surface S by means of the dynamic pressure stabilizing plate 5 in mutually stacked condition, and, the conductive gel sheets 3, 4 are interposed between these electrodes 1 and 2 and between the electrode 2 and the skin surface S respectively. Therefore, the two sheets of electrodes 1, 2 are mutually connected in series, and thus the signal is detected and output by using a sufficient area thereof. In this manner, a voltage VN of the body motion noise signal output from the electrode 2 sandwiched in between is decreased by a predetermined ratio defined by the number of the electrodes 1, 2 and the conductive gel sheets 3, 4, i.e., ½ with respect to a voltage 2VN of the body motion noise signal output from the outermost electrode 1.

Therefore, according to the bioelectrode pad of this embodiment, since the outermost electrode 1 is used as the detection electrode of the body motion noise signal and also the inner electrode 2 is used as the detection electrode of the original electrocardiac signal, it is possible to detect the voltage VN of the body motion noise signal and the voltage VHN of the original electrocardiac signal in a sufficient level by means of these electrodes 1 and 2. In addition, it is possible to decrease the voltage VN of the body motion noise signal supplied from the inner electrode 2 by ½ which is a predetermined ratio defined by the number of the electrodes 1, 2 and the conductive gel sheets 3, 4 with respect to a voltage 2VN of the body motion noise signal output from the outermost electrode 1.

Then, in the electrocardiograph of the embodiment mentioned above, the first differential amplifier 11 obtains a difference between the signals supplied from respective electrodes 2 of the two bioelectrode pads of the embodiment mentioned above so as to determine the original electrocardiac signal. Moreover, the second differential amplifiers 12, 13 obtain a difference between the signals supplied from the electrode 1 and 2 with respect to each of the two bioelectrode pads of the embodiment mentioned above so as to determine the body motion noise signal as mentioned above. Then, the body motion noise removing circuit constructed by the two low-pass filters 14, 15 and the two differential amplifiers 16, 17 removes the low frequency component of the body motion noise signals supplied from respective two bioelectrode pads of the embodiment mentioned above from the original electrocardiac signal so as to output an electrocardiac signal. In this case, a level controlling circuit not shown is arranged to an input side of respective differential amplifiers so as to compensate an arbitrary signal by the difference.

Therefore, according to the electrocardiograph of this embodiment, it is possible to obtain the body motion noise signal and the original electrocardiac signal in a sufficient level as mentioned above, and it is possible to easily perform gain settings of the body motion noise signal and the original electrocardiac signal. Therefore, it is possible to sufficiently remove an influence of the body motion from the electrocardiac signal.

Further, according to the bioelectrode pad of this embodiment, since the bioelectrode pad comprises the conductive gel sheet 4 which is stacked in an outer side of a lower side of the two sheets of electrodes 1, 2 in the stacked direction thereof, the conductive gel sheet 4 is interposed between the skin surface S and the electrode 2 arranged nearest to the skin surface S. Therefore, it is possible to detect the voltage VN of the body motion noise signal even by the electrode 2 arranged nearest to the skin surface, and also it is possible to cover the electrode 2 by the conductive gel sheet 4.

Moreover, according to the bioelectrode pad of this embodiment, since the electrode 2 sandwiched between the conductive gel sheets 3, 4 among the two sheets of electrodes 1, 2 has a net-like shape, the properties of the conductive gel sheets 3, 4 arranged at both sides of the electrode 2 become even, due to the penetration of the conductive gel through the net-like electrode 2. Therefore, it is possible to easily perform the gain settings of the body motion noise and the original electrocardiac signal in the electrocardiograph. Moreover, it is possible to increase a contact area between the electrode 2 and the conductive gel sheets 3, 4 as compared with the planar electrode. Further, it is possible to deform the electrode 2 flexibly along the skin surface S. From these points, it is possible to improve a signal detection level.

Then, according to the bioelectrode pad of this embodiment, the bioelectrode pad further comprises the fitting sheet 6 having: the intermediate portion 6b for supporting the dynamic pressure stabilizing plate 5, the electrodes 1, 2 and the conductive gel sheets 3, 4 in a stacked condition, which is stacked outside of the dynamic pressure stabilizing plate 5 in a stacked direction of the two sheets of electrodes 1, 2; and the end portion 6c for fitting the dynamic pressure stabilizing plate 5, the electrodes 1, 2 and the conductive gel sheets 3, 4 supported by the intermediate portion 6b to the skin surface S at a predetermined portion of the living body, which is continued with the intermediate portion 6b and is positioned outside of the dynamic pressure stabilizing plate 5, the electrodes 1, 2 and the conductive gel sheets 3, 4 in an extended direction of the two sheets of electrodes 1, 2 and has the adhesive layer 6a. Therefore, it is possible to securely maintain the dynamic pressure stabilizing plate 5, the electrode 1, 2 and the conductive gel sheets 3, 4 in a staked condition on the skin surface S of the predetermined portion of the living body.

FIGS. 4(a) and 4(b) are a partially-cutout perspective view and a cross-sectional view respectively showing one modified embodiment of the bioelectrode pad of the embodiment mentioned above. In this modified embodiment, the electrode 2 is directly contacted to the skin surface S of a predetermined portion of the living body by omitting the conductive gel sheet 4 of a side of the skin surface S among the two sheets of conductive gel sheets 3, 4, and the other points are constructed in the same manner as those of the embodiment mentioned above.

Also in the construction of this modified embodiment, it is possible to exert the same functions and effects as those of the embodiment mentioned above. Especially, since the electrode 2 among the two sheets of electrodes 1, 2 has a net-like shape, a contact area between the electrode 2 and the conductive gel sheet 3 is increased as compared with the planar electrode by penetrating the conductive gel of the conductive gel sheet 3 through the net-like electrode 2. In addition, the electrode 2 is deformed flexibly along the skin surface S. In this manner, it is possible to improve the detection level of the original electrocardiac signal.

FIG. 5 is a cross-sectional view showing another embodiment of the bioelectrode pad according to the present invention, and the portions in this figure similar to those of the previous embodiment are denoted by the same reference symbols as those of the previous embodiment. The bioelectrode pad according to this embodiment differs from the bioelectrode pad of the previous embodiment in that a third electrode 7 is stacked to a lower side of the lower conductive gel sheet 4 in the bioelectrode pad of the previous embodiment, and the other constructions are same as those of the previous embodiment.

Namely, here, the electrode 7 has a substantially net-like shape formed by for example a metal wire as a whole, and has a connection terminal 7a projected from its upper surface. Moreover, surfaces of the net-like portion and the connection terminal 7a are coated by a plating of for example silver chloride which is a high-conductive material, and an outer surface of a shaft portion of the connection terminal 7a of the electrode 7 is coated by an insulating material. Further, a tip portion of the connection terminal 7a is projected at a surface side of the fitting sheet 6 by penetrating it from a rear side via through holes of the conductive gel sheets 3, 4, the electrodes 1, 2 and the dynamic pressure stabilizing plate 5 and a through hole of the intermediate portion 6b of the fitting sheet 6. Then, the electrode 7 is maintained in a stacked condition with the other electrodes 1, 2 by an adhesive force of the lower conductive gel sheet 4.

FIG. 6 is a block diagram showing a construction of another embodiment of the electrocardiograph according to the present invention which utilizes the bioelectrode pad of the embodiment mentioned above, and the portions in this figure similar to those of the previous embodiment are denoted by the same reference symbols as those of the previous embodiment. In the electrocardiograph of this embodiment, the electrodes 2 of each of the two bioelectrode pads are connected only to the first differential amplifier 11 as the first difference circuit, and the first differential amplifier 11 obtains a difference between the signals supplied from the electrodes 2 of each of the two bioelectrode pads, amplifies the difference and outputs the amplified difference as the original electrocardiac signal. Moreover, the electrodes 1, 7 are connected to the second differential amplifiers 12, 13 respectively as the second difference circuit, and the second differential amplifiers 12, 13 obtain a difference between the signals supplied from the electrodes 1 and 7 of each of the two bioelectrode pads, amplify the difference and output the amplified difference as the body motion noise signal respectively.

In the bioelectrode pad of the embodiment mentioned above, if the bioelectrode pad is applied to a skin surface S of a predetermined portion of the living body as shown in FIG. 7, the three sheets of electrodes 1, 2, 7 of the bioelectrode pad are pressed to the skin surface S by means of the dynamic pressure stabilizing plate 5 in mutually stacked condition, and, the conductive gel sheets 3, 4 are interposed between these electrodes 1 and 2 and between the electrodes 2 and 7 respectively. Therefore, the three sheets of electrodes 1, 2, 7 are mutually connected in series, and thus the signal is detected and output by using a sufficient area respectively. In this manner, the voltage VN of the body motion noise signal output from the electrode 2 sandwiched in between is decreased by a predetermined ratio defined by the number of the electrodes 1, 2, 7 and the conductive gel sheets 3, 4, i.e., ½ with respect to the voltage 2VN of the body motion noise signal output from the outer electrodes 1, 7.

Therefore, according to the bioelectrode pad of this embodiment, since the outer electrodes 1, 7 are used as the detection electrode of the body motion noise signal and also the interposed electrode 2 is used as the detection electrode of the original electrocardiac signal, it is possible to detect the voltage VN of the body motion noise signal and the voltage VHN of the original electrocardiac signal in a sufficient level by means of these electrodes 1, 2, 7. In addition, it is possible to decrease the voltage VN of the body motion noise signal supplied from the interposed electrode 2 by ½ which is a predetermined ratio defined by the number of the electrodes 1, 2, 7 and the conductive gel sheets 3, 4 with respect to the voltage 2VN of the body motion noise signal output from the outer electrodes 1, 7.

Then, in the electrocardiograph of the embodiment mentioned above, the first differential amplifier 11 obtains a difference between the signals supplied from respective electrodes 2 of the two bioelectrode pads of the embodiment mentioned above so as to determine the original electrocardiac signal. Moreover, the second differential amplifiers 12, 13 obtain a difference between the signals supplied from the electrode 1 and 7 with respect to each of the two bioelectrode pads of the embodiment mentioned above so as to determine the body motion noise signal as mentioned above. Then, the body motion noise removing circuit constructed by the two low-pass filters 14, 15 and the two differential amplifiers 16, 17 removes the low frequency component of the body motion noise signals supplied from respective two bioelectrode pads of the embodiment mentioned above from the original electrocardiac signal so as to output the electrocardiac signal. In this case, a level controlling circuit not shown is arranged to an input side of respective differential amplifiers so as to compensate an arbitrary signal by the difference.

Therefore, according to the electrocardiograph of this embodiment, as is the same as the previous embodiment, it is possible to obtain the body motion noise signal and the original electrocardiac signal in a sufficient level as mentioned above, and it is possible to perform gain settings of the body motion noise signal and the original electrocardiac signal in an easier manner than that of the previous embodiment. Therefore, it is possible to sufficiently remove an influence of the body motion from the electrocardiac signal.

FIG. 8 is a schematic view showing a measurement result of the electrocardiac signal by means of the electrocardiograph of the embodiment illustrated in FIG. 6. In this figure, a symbol SHN indicates a signal due to the voltage VHN of the original electrocardiac signal, SN indicates a signal due to the voltage VN of the body motion noise signal, and SH indicates a signal due to the voltage VH of the electrocardiac signal respectively. As is clearly understood from FIG. 8, according to the electrocardiograph of the embodiment mentioned above, it is possible to output an extremely clear electrocardiac signal from which an influence of the body motion is removed sufficiently.

Hereinbefore, the explanation is performed on the basis of the embodiment shown in the drawings. However, the present invention is not limited to the embodiments mentioned above, but various suitable alterations are possible within the scope of the descriptions of claims. In the bioelectrode pad according to the present invention, for example, the fitting sheet 6 and the peeling sheet are omitted, and a stacked member formed by the dynamic pressure stabilizing plate 5, the electrodes 1, 2, the conductive gel sheets 3, 4 and the like may be fitted on the skin surface S by means of an adhesive tape and the like. Moreover, the electrodes 2, 7 may be formed by a flexible porous member such as a fabric-like member and the like, or a rigid porous member, or a plate with no holes without using the net-like member. Further, the dynamic pressure stabilizing plate 5 may be made by a soft member, or the electrode 1 may be used also as the dynamic pressure stabilizing plate without using the dynamic pressure stabilizing plate 5. In this case, the electrode 1 may be made of a flexible member having a net-like shape and the like.

Moreover, in the electrocardiograph of the present invention, for example, the electrode 1 may be used as the detection electrode of the original electrocardiac signal, while the electrode 2 may be used as the detection electrode of the body motion noise signal. Further, as is the same as the conventional embodiment, a myoelectric noise may be removed from the original electrocardiac signal by using an indifferent electrode connected to a ground circuit and a high-pass filter.

INDUSTRIAL APPLICABILITY

As mentioned above, according to the bioelectrode pad of the present invention, for example, if the electrode at the outer side of the opposite side with respect to the skin side is used as the detection electrode of the body motion noise signal and the electrode sandwiched between the electrode and the skin is used as the detection electrode of the original electrocardiac signal, or, if the electrode at the outer side of the opposite side with respect to the skin side is used as the detection electrode of the original electrocardiac signal and the electrode sandwiched between the electrode and the skin is used as the detection electrode of the body motion noise signal, the body motion noise signal and the original electrocardiac signal can be detected respectively in a sufficient level by using these electrodes. Moreover, the signal supplied from the electrode sandwiched between the electrode and the skin can be decreased by a predetermined ratio defined by the number of the electrodes and the conductive gel sheets with respect to the voltage of the signal output from the electrode at the outer side of the opposite side with respect to the skin side.

Moreover, according to the electrocardiograph of the present invention utilizing the bioelectrode pad of the present invention, it is possible to easily obtain the body motion noise signal and the original electrocardiac signal in a sufficient level as mentioned above. In addition, it is possible to easily perform the gain settings of the body motion noise signal and the original electrocardiac signal. Therefore, it is possible to sufficiently remove an influence of the body motion from the electrocardiac signal.

EXPLANATION OF SYMBOL 1, 2, 7 electrode
1a, 2a, 7a connection terminal
3, 4 conductive gel sheet
5 dynamic pressure stabilizing plate
6 fitting sheet
6a adhesive layer
6b intermediate portion
6c external end portion
11 first differential amplifier
12, 13 second differential amplifier
14, 15 low-pass filter
16, 17 differential amplifier
S skin surface

The invention claimed is:

1. An apparatus for measuring an electrocardiac signal comprising:
   a plurality of bioelectrode pads adapted to apply to a skin of a living body, each of the plurality of bioelectrode pads including:
   a plurality of electrode sheets mutually stacked, the plurality of electrode sheets including an outermost electrode sheet positioned farthest from the skin and an inner electrode sheet positioned nearer from the skin than the outermost electrode sheet, each of the plurality of electrode sheets having an independent electrical connector; and
   at least one conductive gel sheet arranged alternately with the plurality of electrode sheets and each of the at least one conductive gel sheet being interposed between adjacent two of the plurality of electrode sheets among the plurality of electrode sheets, at least one electrode sheet has a shape different from another of the plurality of electrode sheets, and the at least one electrode sheet having a different shape has a net-like shape or a porous shape; and
   an electrocardiograph for measuring an electrocardiac signal by processing an electrical signal detected by the plurality of bioelectrode pads, the electrocardiograph including:
   a first difference circuit for determining an original electrocardiac signal by obtaining a difference between signals supplied respectively from the inner electrode sheet among the plurality of electrode sheets in one of the plurality of bioelectrode pads and the inner electrode sheet among the plurality of electrode sheets in another one of the plurality of bioelectrode pads;
   a second difference circuit for determining a body motion noise signal by obtaining a difference between signals supplied respectively from two of the plurality of electrode sheets in either one of the plurality of bioelectrode pads, the two electrode sheets including at least the outermost electrode sheet; and
   a body motion noise removing circuit for removing from the original electrocardiac signal a low frequency component of the body motion noise signals supplied from the second difference circuit for either one of the plurality of bioelectrode pads.

2. An apparatus for measuring an electrocardiac signal comprising:
   a plurality of bioelectrode pads adapted to apply to a skin of a living body, each of the plurality of bioelectrode pads including:
   a plurality of electrode sheets mutually stacked, the plurality of electrode sheets including an outermost electrode sheet positioned farthest from the skin and an inner electrode sheet positioned nearer from the skin than the outermost electrode sheet, each of the plurality of electrode sheets having an independent electrical connector, the plurality of electrode sheets includes three electrode sheets stacked with each other; and
   at least one conductive gel sheet arranged alternately with the plurality of electrode sheets and each of the at least one conductive gel sheet being interposed between adjacent two of the plurality of electrode sheets among the plurality of electrode sheets, at least one electrode sheet has a shape different from another of the plurality of electrode sheets, and the at least one electrode sheet having a different shape has a net-like shape or a porous shape; and an electrocardiograph for measuring an electrocardiac signal by processing an electrical signal detected by the plurality of bioelectrode pads, the electrocardiograph including:
a first difference circuit for determining an original electrocardiac signal by obtaining a difference between signals supplied respectively from the inner electrode sheet among the plurality of electrode sheets in one of the plurality of bioelectrode pads and the inner electrode sheet among the plurality of electrode sheets in another one of the plurality of bioelectrode pads;
a second difference circuit for determining a body motion noise signal by obtaining a difference between signals supplied respectively from two of the plurality of electrode sheets in either one of the plurality of bioelectrode pads, the two electrode sheets including at least the outermost electrode sheet; and
a body motion noise removing circuit for removing from the original electrocardiac signal a low frequency component of the body motion noise signals supplied from the second difference circuit for either one of the plurality of bioelectrode pads.

3. The apparatus of claim 2, wherein:
the first difference circuit determines the original electrocardiac signal by obtaining the difference between signals supplied respectively from the inner electrode sheet among the three electrode sheets positioned between two other electrode sheets of the plurality of three electrode sheets, and
the second difference circuit determines the body motion noise signal by obtaining the difference between signals supplied respectively from the two other electrode sheets of the three electrode sheets, the two other electrode sheets including at least the outermost electrode sheet.

4. An apparatus for measuring an electrocardiac signal comprising:
a plurality of bioelectrode pads adapted to apply to a skin of a living body, each of the plurality of bioelectrode pads including:
a plurality of electrode sheets mutually stacked, the plurality of electrode sheets including an outermost electrode sheet positioned farthest from the skin and an inner electrode sheet positioned nearer from the skin than the outermost electrode sheet, each electrode sheet of the plurality of electrode sheets having an independent electrical connector, the plurality of electrode sheets includes three electrode sheets stacked with each other;
at least one conductive gel sheet arranged alternately with the plurality of electrode sheets and each of the at least one conductive gel sheet being interposed between adjacent two of the plurality of electrode sheets; and
a conductive gel sheet stacked with the plurality of electrode sheets at an outside of the plurality of electrode sheets and arranged at a side adapted to face the skin in a stacked direction of the plurality of electrode sheets among the plurality of electrode sheets, at least one electrode sheet has a shape different from another of the plurality of electrode sheets, and the at least one electrode sheet having a different shape has a net-like shape or a porous shape; and
an electrocardiograph for measuring an electrocardiac signal by processing an electrical signal detected by the plurality of bioelectrode pads, the electrocardiograph including:
a first difference circuit for determining an original electrocardiac signal by obtaining a difference between signals supplied respectively from the inner electrode sheet among the plurality of electrode sheet of sheets in one of the plurality of bioelectrode pads and the inner electrode sheet among the plurality of electrode sheets in another one of the plurality of bioelectrode pads;
a second difference circuit for determining a body motion noise signal by obtaining a difference between signals supplied respectively from two of the plurality of electrode sheets in either one of the plurality of bioelectrode pads, the two electrode sheets including at least the outermost electrode sheet; and
a body motion noise removing circuit for removing from the original electrocardiac signal a low frequency component of the body motion noise signal supplied from the second difference circuit for either one the plurality of bioelectrode pads.

5. The apparatus of claim 4, wherein:
the first difference circuit determines the original electrocardiac signal by obtaining the difference between signals supplied respectively from the inner electrode sheet among one of the three electrode sheets positioned between two other electrode sheets of the three electrode sheets, and
the second difference circuit determines the body motion noise signal by obtaining the difference between signals supplied respectively from the two other electrode sheets of the three electrode sheets, the two other electrode sheets including at least the outermost electrode sheet.

* * * * *